(12) United States Patent  
Brannon et al.

(10) Patent No.: US 8,313,229 B2
(45) Date of Patent: Nov. 20, 2012

(54) AGITATION SYSTEM AND METHOD FOR MEASURING SETTLING RATE OF SOLIDS FROM A SUSPENSION

(75) Inventors: Michael Joe Brannon, Gray, TN (US); Craig Alan Schmidt, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 185 days.

(21) Appl. No.: 12/767,360

(22) Filed: Apr. 26, 2010

(65) Prior Publication Data

US 2010/0202245 A1    Aug. 12, 2010

Related U.S. Application Data

(62) Division of application No. 11/503,772, filed on Aug. 14, 2006, now abandoned.

(51) Int. Cl.
*B01F 3/14* (2006.01)
*B01F 15/00* (2006.01)
*G01M 1/00* (2006.01)

(52) U.S. Cl. .............. 366/142; 366/150.1; 366/279; 366/340; 366/349; 366/601

(58) Field of Classification Search ........... 73/54.28, 73/54.07, 32 A, 31, 61.63, 61.65, 54.19, 54.13; 366/142, 150.1, 279, 348, 349, 601
See application file for complete search history.

(56) References Cited

U.S. PATENT DOCUMENTS

| | | | |
|---|---|---|---|
| 1,756,286 A | 4/1930 | Farrall et al. | |
| 1,840,101 A | 1/1932 | Jespersen | |
| 1,892,839 A | 1/1933 | Howard | |
| 2,122,765 A | 7/1938 | Weiler | |
| 2,266,733 A | 12/1941 | Bays et al. | |
| 2,316,570 A | 4/1943 | Dunham | |
| 2,339,991 A | 1/1944 | Hagy | |
| 2,354,923 A * | 8/1944 | McNamee | 73/54.28 |
| 2,452,142 A | 10/1948 | Pecker | |
| 2,736,195 A * | 2/1956 | Christianson | 73/843 |
| 2,904,401 A | 9/1959 | Booth | |
| 3,030,790 A | 4/1962 | Davenport et al | |
| 3,053,078 A * | 9/1962 | Jewett | 73/53.01 |
| 3,269,171 A | 8/1966 | Bruss et al. | |
| 3,285,057 A | 11/1966 | Zurik | |
| 3,803,903 A | 4/1974 | Lin | |

(Continued)

FOREIGN PATENT DOCUMENTS

EP 0 555 902 8/1993

(Continued)

*Primary Examiner* — Tony G Soohoo
(74) *Attorney, Agent, or Firm* — Jennifer R. Knight

(57) ABSTRACT

An agitation system including a motor that is capable of measuring the torque output of the motor required to mix a suspension. The motor is attached to an agitator which is placed in a suspension to be measured. The agitator is placed in the suspension and the agitation system is turned on for a period of time. This period determined by the type of agitator used and the characteristics of the suspension. When the suspension is well mixed and the torque measurement on the agitator becomes stable, the agitation system is stopped. The suspension is allowed to sit without agitation for a period of time and the agitation system is started again. After a period of time the agitation system is started and the amount of torque needed to begin turning the agitator is measured.

8 Claims, 4 Drawing Sheets

INCREASING SETTING TIME MODE

U.S. PATENT DOCUMENTS

| | | | |
|---|---|---|---|
| 3,920,227 A | 11/1975 | Davis, Jr. | |
| 4,008,093 A | 2/1977 | Kitsuda et al. | |
| 4,181,023 A | 1/1980 | Clamroth et al. | |
| 4,281,288 A | 7/1981 | Izumi | |
| 4,283,938 A | 8/1981 | Epper et al. | |
| 4,318,177 A | 3/1982 | Rapp et al. | |
| 4,466,276 A | 8/1984 | Ruyak et al. | |
| 4,544,275 A | 10/1985 | Hudelmaier | |
| 4,571,988 A | 2/1986 | Murphy, Jr. | |
| 4,578,246 A | 3/1986 | Pope | |
| 4,592,226 A | 6/1986 | Weber et al. | |
| 4,622,846 A | 11/1986 | Moon, Jr. et al. | |
| 4,648,264 A | 3/1987 | Freese et al. | |
| 4,687,490 A | 8/1987 | Heaton, III et al. | |
| 4,779,186 A | 10/1988 | Handke et al. | |
| 4,836,686 A | 6/1989 | Sukup | |
| 4,900,154 A | 2/1990 | Waitzinger et al. | |
| 4,904,277 A | 2/1990 | Najjar et al. | |
| 4,938,605 A | 7/1990 | Friedrich | |
| 4,950,307 A | 8/1990 | Najjar et al. | |
| 5,056,358 A * | 10/1991 | Laskowski et al. | 73/54.28 |
| H0001161 H * | 4/1993 | Berggren et al. | 44/280 |
| H1161 H | 4/1993 | Berggren et al. | |
| 5,315,864 A | 5/1994 | Surjaatmadja et al. | |
| 5,321,974 A | 6/1994 | Hemmings et al. | |
| 5,365,777 A | 11/1994 | Layton | |
| 5,401,402 A | 3/1995 | Christy et al. | |
| 5,513,912 A | 5/1996 | Lotz et al. | |
| 5,541,855 A | 7/1996 | Enzler et al. | |
| 5,546,791 A | 8/1996 | Meeten | |
| 5,604,300 A | 2/1997 | Sayers et al. | |
| 5,684,247 A | 11/1997 | Preikschat | |
| 5,713,663 A | 2/1998 | Zandberg et al. | |
| 5,799,734 A * | 9/1998 | Norman et al. | 166/278 |
| 5,906,432 A | 5/1999 | Wade et al. | |
| 5,992,223 A | 11/1999 | Sabins et al. | |
| 6,450,013 B1 * | 9/2002 | Gallagher | 73/54.25 |
| 6,537,819 B2 * | 3/2003 | Cohen et al. | 436/69 |
| 6,584,833 B1 * | 7/2003 | Jamison et al. | 73/61.63 |
| 6,782,735 B2 * | 8/2004 | Walters et al. | 73/54.28 |
| 6,808,305 B2 | 10/2004 | Sharpe et al. | |
| 6,874,353 B2 | 4/2005 | Johnson et al. | |
| 6,931,916 B2 * | 8/2005 | Zamora et al. | 73/61.63 |
| 7,014,775 B2 | 3/2006 | Sharpe et al. | |
| 7,201,040 B2 * | 4/2007 | Bateson et al. | 73/54.28 |
| 7,384,180 B2 | 6/2008 | Jarvinen et al. | |
| 7,392,842 B2 | 7/2008 | Morgan et al. | |
| 7,575,365 B2 | 8/2009 | Jung | |
| 7,632,007 B2 | 12/2009 | Wulf et al. | |
| 7,712,526 B2 * | 5/2010 | Morgan et al. | 166/250.1 |
| 2003/0136184 A1 * | 7/2003 | Walters et al. | 73/54.28 |
| 2004/0149019 A1 * | 8/2004 | Johnson et al. | 73/54.28 |
| 2006/0203610 A1 | 9/2006 | Bohannon, Jr. et al. | |
| 2007/0251596 A1 | 11/2007 | Scherzer et al. | |
| 2009/0109792 A1 | 4/2009 | Ciancimino et al. | |
| 2009/0110788 A1 | 4/2009 | Ciancimino et al. | |
| 2010/0018294 A1 * | 1/2010 | Tonmukayakul et al. | 73/54.28 |

FOREIGN PATENT DOCUMENTS

JP         59159897         9/1984

* cited by examiner

ABDULrashidedAGITATION SYSTEM AND METHOD FOR
MEASURING SETTLING RATE OF SOLIDS
FROM A SUSPENSION

CROSS-REFERENCE TO RELATED
APPLICATION

This application is a divisional of U.S. patent application Ser. No. 11/503,772, filed on Aug. 14, 2006, the disclosure of which is incorporated herein by reference in its entirety.

FIELD OF THE INVENTION

The present invention relates generally to a system and method for measuring a settling rate of solids from a suspension. The system and method of the present invention enable the user to determine the optimal solids concentration, particle size distribution, pH, additive composition and concentration and other factors for a suspension to thereby optimize the suspension of the solids in solution and obtain the desired flow characteristics.

BACKGROUND OF THE INVENTION

Many industries such as chemical manufacturing, power generation, mining, the oil industry, along with numerous others, have occasion to suspend solid particles in some type of fluid. For example, a high fuel-value coal-water suspension (or slurry) that can be injected directly into a furnace as a combustible fuel can be used to replace large quantities of fuel oil. Generally, it is highly desirable that the production time, expense, and amounts of carrier solvents and additives of such suspensions (or slurries) be minimized as much as possible.

Often, for efficient practical use, the suspension must have several essential characteristics. It must have long-term static stability so that it can be stored for extended periods of time by suppliers or at the point of use. During such storage, the slurry must remain uniformly dispersed or, at most, be subject to some soft subsidence which can be easily redispersed by stirring.

With respect to solid fuels used for processes such as power generation or chemical processing, uniform solid dispersion is essential for a reliable fuel source. Such processes can require various concentrations of the solid fuel in a liquid medium (e.g. a slurry). The liquid medium can be any suitable liquid carrier that is beneficial for the specific process. Requirements and process optimization can require varying concentrations of the solid material in the liquid carrier. Thus, in certain applications, reducing the liquid portion of the suspension is desired. However, the suspension must also be sufficiently fluid; that is, have a sufficiently low viscosity, to be pumped to and distributed into the next processing stage.

In order to increase the solids concentration of a suspension, the skilled artisan may use a dispersant such as pH modifiers and the sulfonate salts of ligands, naphthalenes, polystyrenes, polymethacrylates and polyolefins or other suitable dispersants. Such modifiers not only allow for increased solid concentration, but also serve to reduce viscosity. However, when using such modifiers, it is useful and often necessary to determine the optimal type and amount of modifier to achieve the desired effect. For example, if too much modifier is used, the suspension can become unstable and the solids can separate from the liquid.

Various methods have been developed to measure the rates at which particles settle out of suspension. Some of these methods involved visually observing the rates at which the particles settled to the bottom of the container or using some type of detector to measure the settling of the particles. These methods often did not work well when the fluid was opaque or there were large numbers of fine particles that made visual observation or measurement with some type of light detector impractical.

The present invention addresses the above problems by enabling the user to determine the settling rates of solids in a suspension (e.g., a slurry). The present invention also enables the user to determine whether, and how much, modifier should be used. Moreover, the system and method of the present invention does not hamper the ability to observe or measure the rate of particle settling visually or optically. While the examples show the present invention in relation to coal slurries, the invention would be equally useful to other applications involving the suspension of particles in a liquid.

SUMMARY OF THE INVENTION

An embodiment of the present invention concerns a system for measuring the settling rate of solids from a suspension. The system comprises a motor unit, an agitator attached to the motor unit via an attachment rod, a container into which the suspension and the agitator are inserted, and a control unit for controlling activation of the motor unit.

Another embodiment concerns a system for measuring the settling rate of solids from a suspension, comprising a motor unit, an agitator attached to the motor unit via an attachment rod, a container into which the suspension and the agitator are inserted, and an additive feed system for adding additive to the container.

Yet another embodiment concerns a method for determining the settling rate of solids in a suspension, comprising inserting an agitator, connected to a motor unit, into a suspension sample, said suspension being in a container, agitating said suspension for a first period of time until solids in said suspension are uniformly dispersed in the liquid, stopping said agitating for a second period of time to allow the solids to settle, agitating said suspension after said second period of time, and measuring an amount of torque required to start the agitator after said second period of time.

Still another embodiment concerns a method for optimizing a suspension of solids in a solution, comprising inserting an agitator, connected to a motor unit, into a suspension sample, said suspension being in a container, agitating said suspension for a first period of time until solids in said suspension are uniformly dispersed in the liquid, adding at least one or more additive(s) to said suspension, agitating said suspension after said additive or solid is added until the additive is well dispersed, stopping said agitating for a second period of time to allow the solids to settle, and measuring an amount of torque required to start the agitator after said additive(s) is added to thereby determine an optimal amount of at least one of said additive in said suspension.

DETAILED DESCRIPTION OF THE INVENTION

Figure 1:
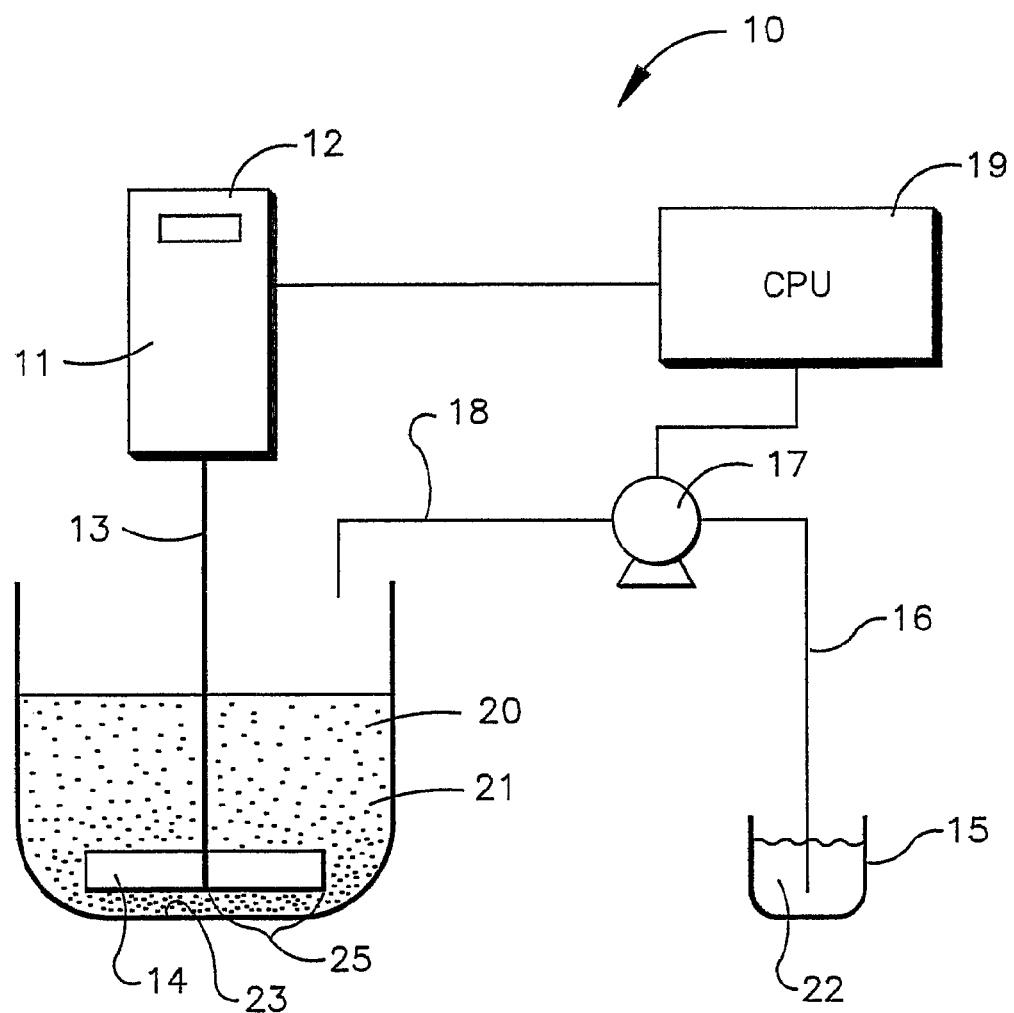
FIG. 1 is a schematic diagram of a settling rate measuring system according to the present invention.

The present invention concerns an agitation system including a system that is capable of measuring the torque output of the motor required to mix a suspension and related methods of use. The motor is attached to an agitator which is placed in a suspension to be measured. The motor is then turned on for a period of time. The time period can be determined by the type of agitator used and the characteristics of the suspension. When the suspension is well mixed and the torque measurement on the motor becomes stable, the agitation system is stopped. The suspension is allowed to sit without agitation for a period of time and the agitation system is started again and the amount of torque needed to begin turning the agitator is measured The various parts of the settling rate measuring system according to the present invention are exemplified in FIG. 1. The system 10 includes an agitator 14 attached to a motor unit 11 via an attachment rod 13. The motor unit 11 is capable of measuring the torque output of the motor and includes a display 12 for showing the torque measurement. Such motor units 11 (e.g., motor units that measure torque and have a display feature), agitators 14 and connecting rods 13 are known to those of ordinary skill in the art (Cole-Parmer®, Servodyne® Mixers, Lightin® Labmaster™ Mixers, GK Heller® Mixers). Moreover, the motor unit 11 should be selected so that it is suitable to the materials and viscosity levels to be measured. The system 10 can also include an additive feed system 17, for adding a desired additive, and an additive reservoir 15. The additive feed system 17 withdraws additive from the additive reservoir 15 via a tube 16 and delivers the additive to a container 20 containing the suspension 21 to be tested via tube 18. The container can be any suitable container having a bottom 23 and sides (such as a beaker) so that it can adequately hold the suspension 21 without spilling. Moreover, an additive feed system 17, and associated connecting tubes 16 and 18, which can be used in the present system are also known to those of ordinary skill. For example, the system can include pressurized reservoir with a valve that can be opened to supply additive to the slurry container or a pump such as a FMI®, Pulsafeeder® or a Milton Roy® metering pump, to supply additive to the slurry container.

The motor unit 11 and additive reservoir 15 can be controlled by a programmable control unit 19 (for example, a central processing unit (CPU)). The control unit 19 can be programmed when the system 10 is built and/or by the end user to turn the motor unit 11 on and off at various time intervals and/or to control the additive feed pump 17 to introduce an additive 22 at a desired rate.

In one embodiment, when system 10 is in use, the agitator 14 is placed near or adjacent the bottom 23 of a container 20 containing a suspension 21 to be tested. In one embodiment, the agitator 14 has at least one flat radial blade 25. However, the design of the agitator 14 may be modified depending on the type of solids and liquid to be tested.

The present invention also relates to a method for determining the settling rate of a suspension over a period of time. In such a method, the agitator 14 is started and the suspension stirred for a period of time (e.g., a first period of time) until all of the solids are well dispersed in the liquid. At this time, the agitation is stopped and the particles allowed to settle for a period of time (e.g., a second period of time). After the period of time has elapsed, the agitator 14 is started and the amount of torque required to start the agitator is observed. The suspension is agitated until the particles are again dispersed in the fluid.

The agitator is then stopped and the particles allowed to settle for another time period (e.g., a third period of time) of time which is normally a longer period of time than the second time period. After the selected period of time has elapsed, the agitator 14 is started and the amount of torque required to start the agitator is observed.

Figure 2:
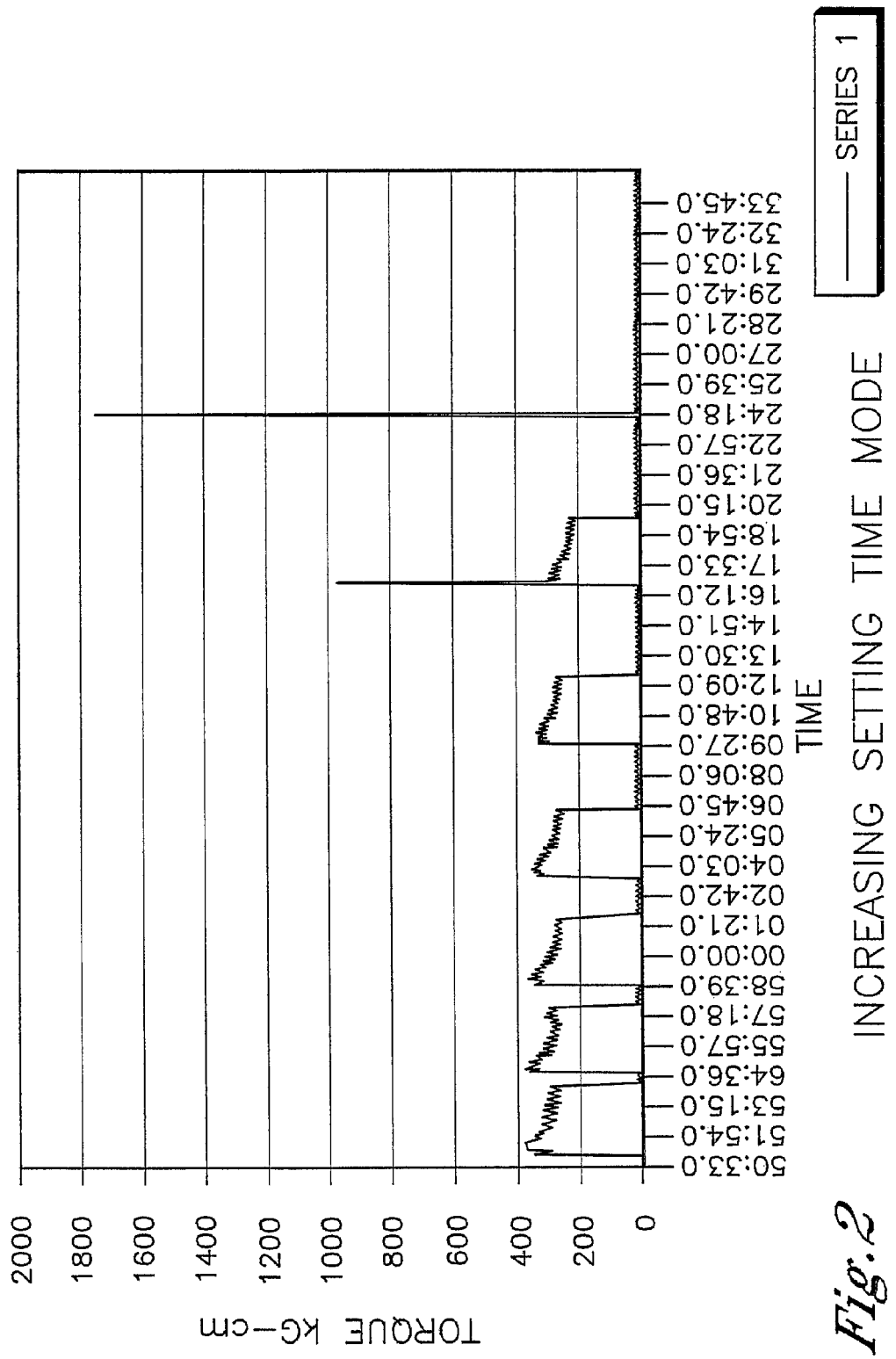
FIG. 2 is a graph showing the torque required to restart the measuring system agitator after progressively longer particle settling time periods.

This procedure can be repeated several times allowing increasing amounts of time for the particles to settle after the agitator is turned off. The process is repeated until the desired time range for settling is reached or a maximum allowable torque to restart the agitator is reached. The graph of FIG. 2 shows the torque required to restart the agitator 14 after increasingly longer particle settling time periods of a coal and water suspension according to the above described method. The time periods measured and the torque will vary greatly depending on the properties of the suspension that is being measured. This data can be used to correlate the changes in start-up torque vs. the time allowed for the particles to settle.

Another method according to the present invention enables a determination of effects of changes in suspension on settling properties. In this method, the agitator 14 is started and allowed to stir the suspension until the particles are well dispersed.

The suspension is then modified in some way, for example, by the addition of more solids (particles) or liquid to change the concentration or by the addition of some other component (e.g. a suspension modifying additive). Dispersants known to those of ordinary skill in the art include pH modifiers and the sulfonate salts of ligands, napthalenes, polystyrenes, polymethacrylates and polyolefins are also used. The agitator 14 is then stopped and the particles allowed to settle for a period of time. The agitator 14 is then started and the amount of torque required to start the agitator 14 is observed.

The process is then repeated by agitating the suspension until the particles are well dispersed additional additive(s) are charged and dispersed and then stopping the agitator 14 for the same period of time. The agitator 14 is then started and the amount of torque required to start the agitator is observed.

Figure 3:
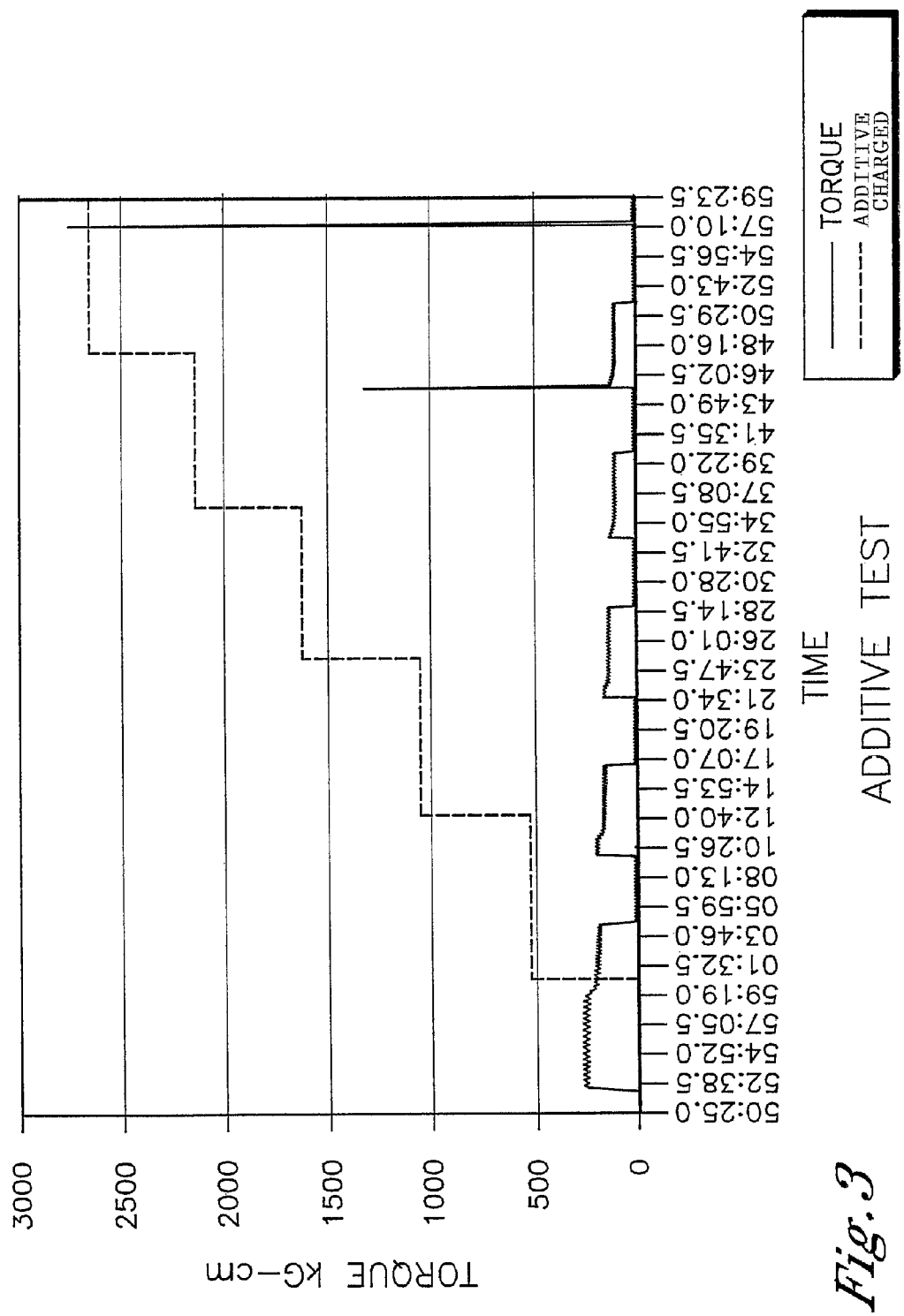
FIG. 3 is a graph showing the effect that adding increasing amounts of additive to the suspension has on the torque required to restart the measuring system agitator.

This process can be repeated as many times as desired to observe the effects of incrementally adding increasing amounts of the solid, liquid, or some other additive to the suspension and observing the change of the start-up torque in relation to the amount of the material that was added. The graph of FIG. 3 shows the effect adding increasing amounts of dispersant to the suspension has on the torque required to restart the measuring system agitator according to this method.

The method according to this particular embodiment enables suspension optimization in that the method enables the determination of the optimal amount of a particular additive for improving the suspension properties (e.g., increased solids/decreased liquid amounts while maintaining good suspension time and flowability of the suspension) and at what amount the additive causes the suspension to separate.

Yet another method of the present invention combines the first two methods described above. In this third method, the start-up torque required for a suspension is measured over several different settling times and then some additive is added. The suspension can also then be tested over the same several periods of settling time. Additional additive is added and the process is repeated to cover the range of settling times and amounts of additive desired.

Although all three of these methods can be done manually by simply turning the agitator on and off at the specified times, observing the agitator torque and recording the torque measurement, and charging the additives as desired, the system 10 can be automated (for example, via use of a CPU) so that all, or part of these functions can be done automatically and the data recorded.

EXAMPLE

Figure 4:
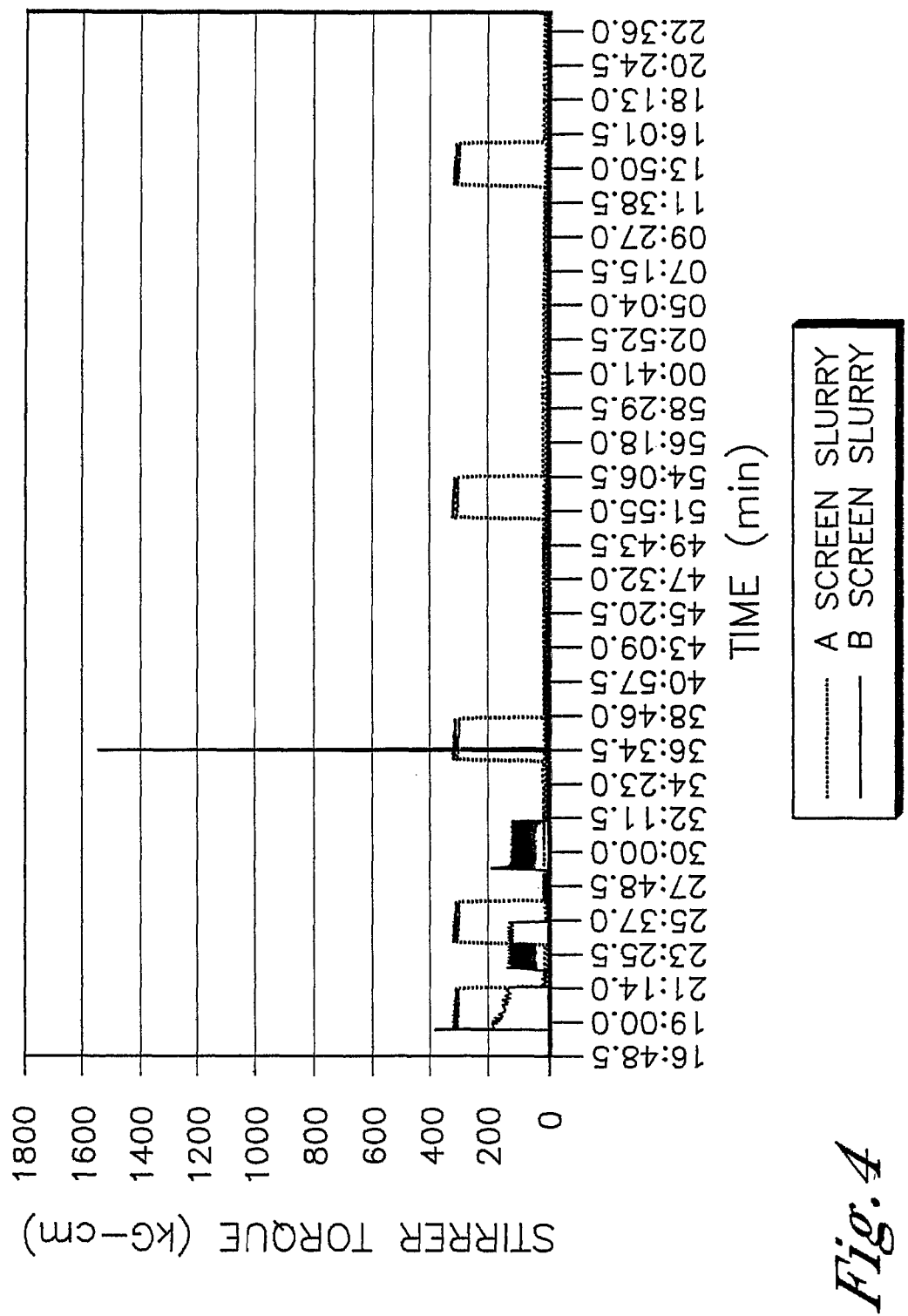
FIG. 4 is a graph showing the torque required to restart the measuring system agitator after increasingly longer particle settling time periods for two samples each prepared in a different manner.

Two different suspensions (slurries) of coal were obtained from plant processing equipment (i.e. rod mill). Each suspension was mixed well and subjected to a test in which each suspension was stirred until it was well dispersed, the agitator stopped and then allowed to settle for a period of time. The agitator was then started and the amount of torque required to start the agitator was measured. The process was then repeated except the time which the suspension was allowed to settle was increased. The length of the settling time was increased until the torque required to start the agitator exceeded 1500 kg-cm. The first sample is labeled as Sample A in FIG. 4. Sample A exceeded the 1500 kg-cm starting torque limit when the settling time was increased to approximately 5 minutes. The second plant sample consisting of the same coal as Sample A but prepared in a different manner did not exceed the 1500 kg-cm limit even when the settling time had increased to over 18 minutes.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

We claim:

1. A method for determining a maximum allowable torque for agitating solids in a suspension, comprising:
    a) inserting an agitator, connected to a motor unit, into a suspension sample, said sample being in a container;
    b) agitating said suspension for a first period of time until solids in said suspension are uniformly dispersed in the liquid;
    c) stopping said agitating for a second period of time to allow the solids to settle;
    d) agitating said suspension after said second period of time;
    e) measuring an amount of torque required to start the agitator after said second period of time; and
    f) repeating steps c)-e) until a maximum allowable torque to restart the agitator is reached.

2. The method according to claim 1, wherein steps c)-e) are repeated a plurality of times and wherein said second period of time of step c) is progressively lengthened.

3. The method according to claim 1, wherein steps c)-e) are repeated a plurality of times and wherein an increasing amount of an additive is added during each of said step c).

4. The method according to claim 1, wherein the agitator is inserted into the container so that the agitator is about $1/16$ to $1/4$ in. from a bottom of said container.

5. A method for optimizing a suspension of solids in a solution, comprising:
    a) inserting an agitator, connected to a motor unit, into a suspension sample, said sample being in a container;
    b) agitating said sample for a first period of time until solids in said suspension are uniformly dispersed in the liquid;
    c) stopping said agitating for a second period of time to allow the solids to settle;
    d) adding an amount of at least one of an additive or an additional amount of said solids to said suspension;
    e) agitating said suspension after said at least one of said additive or said additional amount of said solids is added;
    f) measuring an amount of torque required to start the agitator after said at least one of said additive or said additional amount of said solids is added; and
    g) repeating steps c)-f) to thereby determine an optimal amount of said at least one of said additive and said solids in said suspension.

6. The method according to claim 5, wherein steps c)-e) are repeated a plurality of times and wherein said second period of rest of step c) is progressively lengthened.

7. The method according to claim 5, wherein steps c)-e) are repeated a plurality of times and wherein an increasing amount of said at least one of said additive and said solids is added during each of said step c).

8. The method according to claim 5, wherein the agitator is inserted into the container so that it agitator is about $1/16$ to $1/4$ in. from a bottom of said container.

\* \* \* \* \*